United States Patent [19]

Farrell et al.

[11] 4,043,678
[45] Aug. 23, 1977

[54] CUVETTE

[75] Inventors: Gregory A. Farrell; Abraham Gordon, both of Teaneck, N.J.

[73] Assignee: Technicon Instruments Corporation, Tarrytown, N.Y.

[21] Appl. No.: 662,642

[22] Filed: Mar. 1, 1976

[51] Int. Cl.$^2$ ............................................. G01N 1/10
[52] U.S. Cl. .................. 356/246; 23/230 R; 23/259; 250/576; 356/36
[58] Field of Search ............... 356/36, 246; 250/576; 23/230 R, 230 B, 253 R, 259

[56] References Cited

U.S. PATENT DOCUMENTS

| | | | |
|---|---|---|---|
| 3,691,017 | 9/1972 | Brown et al. | 356/246 UX |
| 3,795,451 | 3/1974 | Mailen | 356/246 |
| 3,799,742 | 3/1974 | Coleman | 356/246 X |
| 3,829,223 | 8/1974 | Hamel | 250/576 X |
| 3,961,899 | 6/1976 | Trivedi et al. | 23/259 X |

*Primary Examiner*—John K. Corbin
*Assistant Examiner*—Matthew W. Koren
*Attorney, Agent, or Firm*—S. P. Tedesco; Stephen E. Rockwell

[57] ABSTRACT

A multichamber cuvette for maintaining in independent and separate condition at least two reactants, one of which may be a sample, until such time that it is desired to mix them for reaction with each other for photometric analysis in the cuvette. At least one of the chambers has a pair of optical quality windows aligned with one another for analysis of the then liquid contents extending between the windows. The cuvette body is of upright construction, defining at least two such chambers laterally of one another, open at the top for filling separately or simultaneously, and interconnected adjacent their lower extremities by a passageway of inverted U shape. The passageway is of an effective height exceeding the highest filling level of each chamber by a distance at least as great as any capillary rise in the passageway beyond such level of the particular liquid in that chamber. Accidental mixing of the chamber contents is prevented by entrapment of air in the passageway by the respective liquids in the chambers and partially filling the legs of the passageway. Mixing through the passageway is effected by the forced flow of fluids therethrough from one chamber to the other while one of the chambers is vented to the atmosphere at the top. The passageway is so configured and also dimensioned in cross section as to allow for the free flow of liquid between the chambers.

18 Claims, 10 Drawing Figures

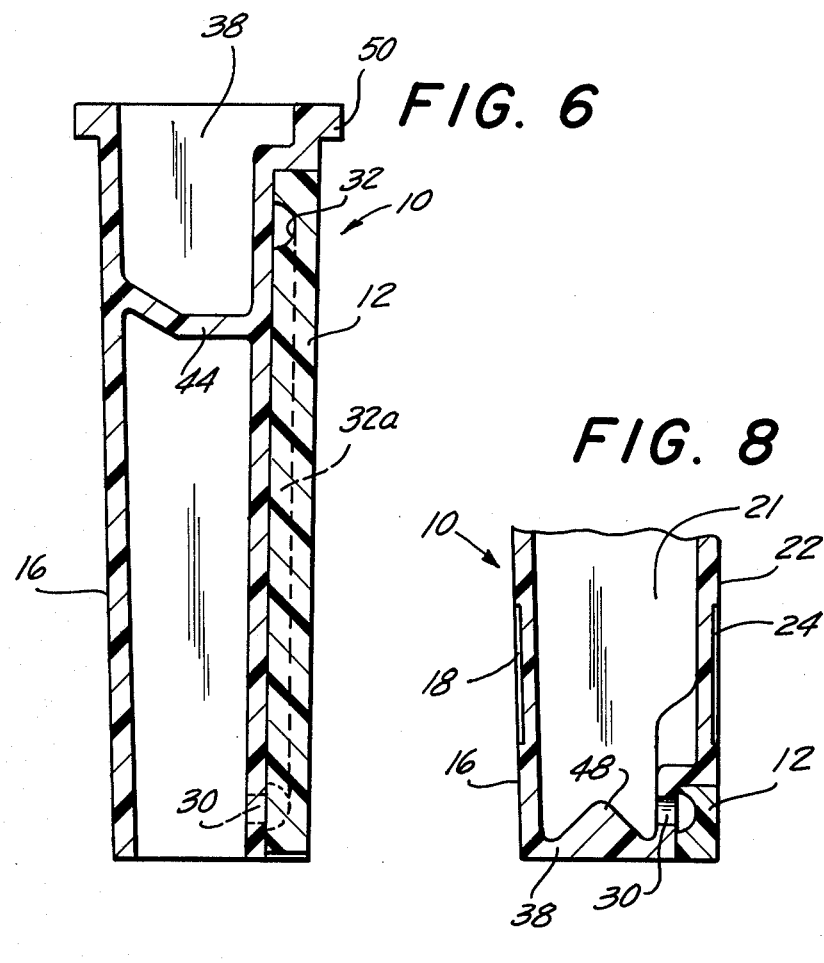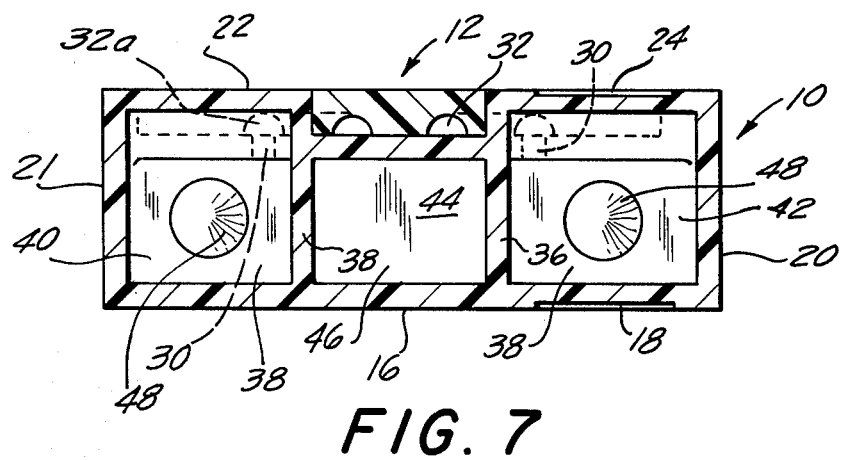

CUVETTE

BACKGROUND OF THE INVENTION

1. Field of the Invention

This invention relates to a multichamber cuvette and relates more particularly to such cuvette which, while not limited thereto, is especially useful in quantitative analysis by optical density of a constituent of body fluids such as blood or urine for example.

2. Prior Art

Brown et al. U.S. Pat. No. 3,691,017 and Mailen U.S. Pat. No. 3,795,451 are typical of the prior art. Brown et al. disclosed a multichamber cuvette for analysis of a constituent of interest in body fluids by an optical density determination in an automated manner. It was disclosed by Brown et al. that a reaction may be measured in the cuvette at one point in its duration or at its end point or a reaction in the cuvette may be temperature- and-time dependent and of the type measured over a period of time to indicate the quantity of the constituent of interest by the rate of the reaction. In accordance with Brown et al., in such kinetic or rate reaction analysis of an enzyme, a trigger or key reactant component, initially located in a first chamber in restricted communication with a second chamber through a passageway, was of a substrate of an enzymatically catalyzed reaction with a reactant component in the second chamber. After a solvent medium had been introduced in the chambers to reconstitute the reagents previously in lyophilized form therein, a liquid sample comprising the catalyzing enzyme was introduced into the second chamber prior to forceful injection thereinto through the aforementioned passageway of the key substance for the reaction to proceed under temperature-controlled conditions.

The cuvette was found to have many drawbacks in practice adversely affecting analysis among which, of a more serious type, were that the cuvette had a lower passageway interconnecting the chambers through which a diluent such as water flowed on reconstitution of the lyophilized reagents. In accordance with Brown et al., only a single diluent injection was utilized to reconstitute the different reagents in both chambers. This injection was made into the second chamber for partial retention therein and partial flow therethrough and through the passageway into the first chamber for retention in the latter, resulting in a high degree of risk of comingling the reagents prior to intentional mixing thereof. This construction and use of the cuvette enabled a small quantity of one of the liquid reagents in one chamber to migrate into and commence reaction with the other liquid reagent in the other chamber during the period of time when it was desired to maintain the last-mentioned liquids in complete isolation from one another, as during incubation, to prevent their premature reaction with one another. It was found that migration by diffusion of only 3% of the reconstituted aforementioned trigger or key component into the aforementioned second chamber was sufficient to invalidate an analysis. Such reagent migration might be occasioned by jarring the cuvette, for example. In view of the foregoing, it will be appreciated that the aforementioned reconstituted reagents in the two chambers of the cuvette were in liquid interfacing relationship in the area of the aforementioned passageway prior to intentional mixing of the reagents, and that such reagent migration discussed above was in fact was likely unless the cuvette was handled with extreme care.

The Mailen U.S. Pat. No. 3,795,451 disclosed a rotor for mixing sample and reagent liquids loaded thereinto for use in a photometric analyzer of the rotary sample-analysis cuvette type. Inner and outer concentric arrays of loading cavities were disposed within the rotor on a one to one basis centripetal to an array of sample analysis cuvettes. Liquid communication was provided by capillary-sized passageways between the respective sample, reagent and analysis cavities and cuvettes upon rotation of the rotor, while intercontact of the liquids in the respective cavities was prevented under static loading conditions. The aforementioned respective passageways between the inner and outer cavities were each provided with an air lock in the form of a bubble trap under static conditions.

The present invention overcomes difficulties in the prior art.

SUMMARY OF THE INVENTION

One object of the invention is to provide a multichamber cuvette having an improved structure for maintaining in independent and separate condition at least two reactants one of which may be a sample, until such time that it is desired to mix them for reaction with each other while in a cuvette for analysis in the cuvette, and which enables a large measure of free flow of the reactants during the mixing thereof. Further, there is provided a cuvette body of upright construction, defining at least two such chambers laterally of one another, open at the top for filling separately or simultaneously, and interconnected adjacent their lower extremities by a passageway of inverted U shape. The passageway is of an effective height exceeding the highest filling level of each chamber by a distance at least as great as any capillary rise in the passageway beyond such level of the particular liquid in that chamber. Accidental mixing of the chambers contents is prevented by entrapped of air in the passageway by the respective liquids in the chambers and partially filling the legs of the passageway. The resistance of the entrapped air to such mixing through the passageway may be overcome at the time mixing is desired by the forced flow of fluid therethrough from one chamber to the other while one of the chambers is vented to the atmosphere. The passageway is so configured and dimensioned in cross-section as to allow for the free flow of liquid between the chambers once the entrapped air in the passageway has been removed.

Other objects of the invention will be apparent from the detailed description of the preferred embodiment of the invention set forth hereinafter.

BRIEF DESCRIPTION OF THE DRAWINGS

In the drawings:

FIGS. 6, 7 and 8 are enlarged sectional views taken on lines 6—6, 7—7, and 8—8, respectively.

DETAILED DESCRIPTION OF THE PREFERRED EMBODIMENTS

Figure 1:
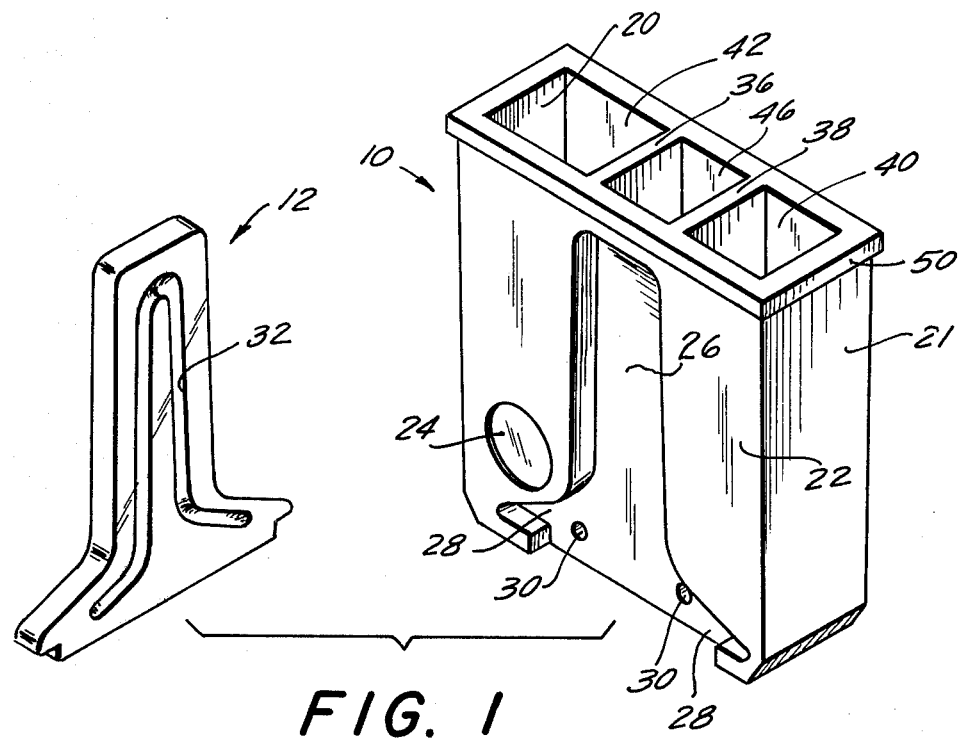
FIG. 1 is an exploded view of a cuvette body embodying the invention.
Figure 2:
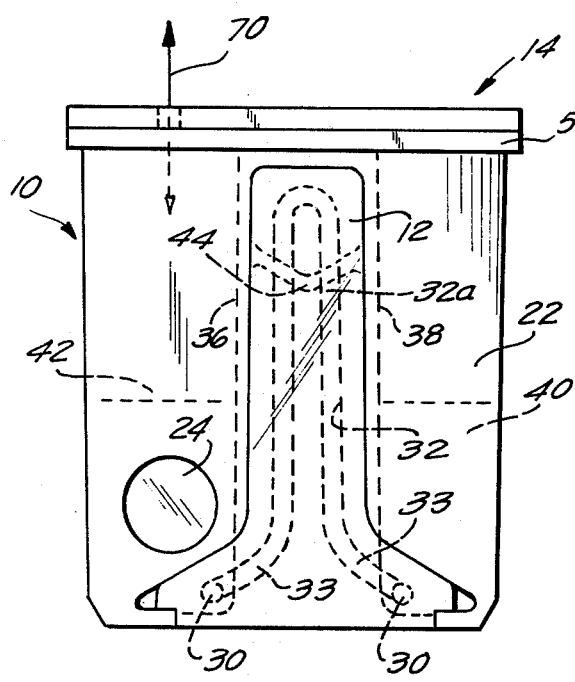
FIG. 2 is a rear elevational view of the cuvette body showing the same with a top cover and illustrating typical liquid levels in two chambers of the body after mixing of such chamber contents.

There is best shown in FIGS. 1 and 2 the general organization of the parts of the cuvette in which the main cuvette body is indicated at 10, a planar rear cover portion of the body at 12 and the top cover of the cuvette at 14. The main body 10 may be molded in one piece of optical grade transparent plastic material. The rear cover portion 12 may also be molded as a single part of suitable plastic material without regard to transparency. The main body 10 has a generally flat, front face 16 (FIG. 7) except in the region of an optical window 18 therein which may be recessed, two sides 20, 21 (FIG. 1), and a rear face 22 (FIGS. 1 and 2) which in its lateral and upper marginal portions is generally flat except in the region of the optical window 24 which may be recessed and is in alignment with the aforementioned window 18. In the generally central region of the rear face 22 there is an upwardly extending recess through the lower extremity thereof to a location approaching the top thereof, which recess is best shown in FIG. 1 and indicated at 26. The recess 26 has the outline indicated in the last mentioned view and receives the complemental rear cover portion 12 of the cuvette body so that the latter is substantially flush with the lateral margins of the rear face of the body in the rear cover portion's assembled condition as shown in FIG. 7. The recess 26 has a pair of wing-like like lateral extensions 28 through each of which extensions 28 there is provided one of a pair of fluid-passing orifices 30 extending through the rear face of the cuvette body. In the assembled cuvette body, the orifices 30 register with the respective legs of an inverted generally U-shaped groove 32 in the near face of the cover portion 12 which groove is preferably semicircular in cross section. In assembled condition, the rear cover portion 12 is suitably welded in place in fluid-and-water-tight relation to the main body to prevent leakage between the latter and rear cover portion 12 and prevent any leakage out of the generally U-shaped passageway 32a (FIG. 4 for example) formed by the orifices 30, the groove 32 in the rear cover portion 12 and the bottom of the recessed portion 26 of the main body.

Figure 3:
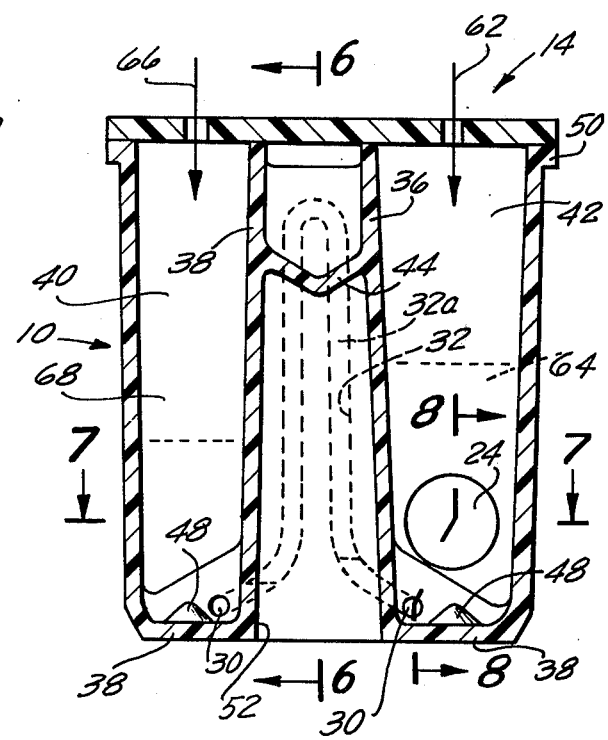
FIG. 3 is a view similar to FIG. 2 but illustrating a front, elevational section of the cuvette and showing typical liquid levels in the two chambers just prior to mixing of the chamber contents.

As shown in FIGS. 1 and 3, the interior of the main body 10 is vertically compartmented by laterally spaced walls 36, 38 extending between the front and rear faces of the cuvette body and which form, together with the near sides of the main body and respective bottom portions 38 extending therebetween, a first upwardly opening first chamber 40 and an upwardly opening second chamber 42. The orifices 30 communicate with the chambers 40, 42, respectively. Intermediate the upper and lower extremities of the walls 36, 38 and extending between these walls is a portion 44 of the main body 10 which forms, together with the front and rear faces of the main body, an upwardly opening chamber 46 between the chambers 40, 42 and which may be relatively shallow as indicated in FIG. 3.

The bottom portions 38 of the chambers 40, 42 have in the central regions thereof, respectively, upwardly projecting cones 48. The main body 10 has a laterally extending lip 50 around the upper extremity thereof to which the cuvette cover 14 is secured. The cover 14 (FIG. 2) is preferably a probe-puncturable laminate which provides a moisture and gas barrier the construction and use of which is not part of the present invention. The chamber 46 may be utilized to hold a liquid sample, for example, prior to deposit of a portion thereof in one of the chambers 40, 42.

As shown in FIG. 2, for example, the lower end portions of the legs of the groove 32 of generally inverted U-shape are gently flared outwardly or inclined as at 33. This permits registration of the leg portions with the respective orifices 30, while enabling narrowing of the upper portion of the inverted U-shaped groove 32 so that it may be laterally separated from the optical window 24, as shown in FIG. 2. The aforementioned gently flared portions 33 of the groove 32 minimizes restriction of flow in the passageway 32a. Further as shown in the last-mentioned view, the top portion of the groove 32 is shaped on a substantial radius so as to minimize restriction of flow in the passageway. The main body 10 and the rear cover portion 12 are so shaped (FIGS. 1 and 2) that the two may be easily assembled. For this purpose, the rear cover portion 12 is placed in parallel, face-to-face relation with the recess 26 and the two parts are brought together. It is to be noted that the configuration of the recess 26 is such as to support the rear cover portion 12 when assembled, that is, the top and lower portions of the recess 26 prevent any relative sliding movement between the main body 10 and the rear cover portion 12 once they are assembled. When the parts are so assembled the orifices 30 register in the aforementioned manner with the groove 32 in the rear cover portion 12.

Figure 4:
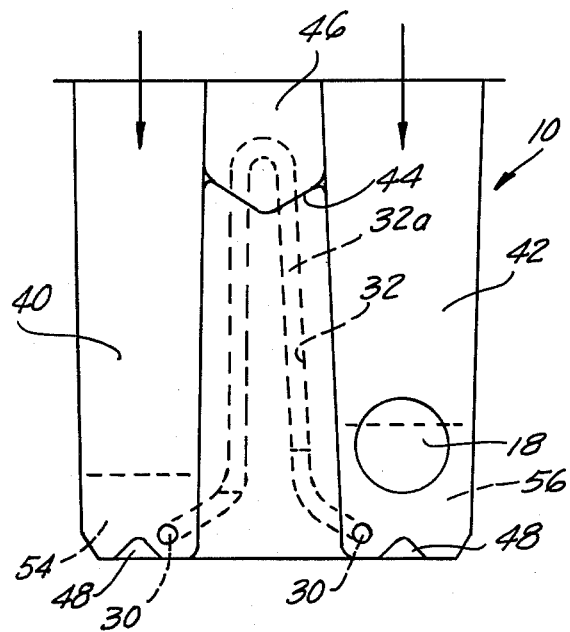
FIG. 4 is a schematic view, similar to FIG. 3, with the top cover removed and illustrating different liquid reagents deposited in the respective chambers prior to lyophilization of such reagents at typical filling heights.
Figure 5:
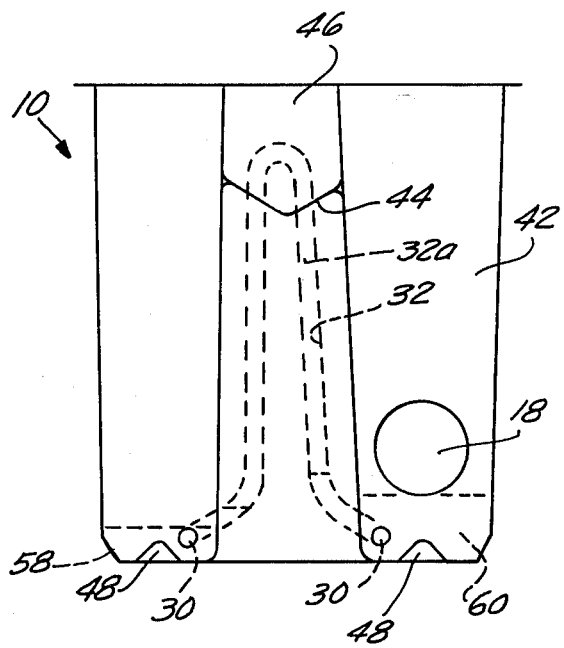
FIG. 5 is a view similar to FIG. 4 showing the reagents in the last mentioned chambers in lyophilized form at typical heights just prior to the application of the top cover to the body.

One type of use to which the cuvette may be put, while not limiting the use thereof, is as follows. Such use may be for the quantitative determination of lactic dehydrogenase in a sample of blood serum. The reagents employed are lactic acid, the key component or trigger for the reaction, and nicotinamide adenine dinucleotide (NAD) with an appropriate buffer (tris [hydroxymethyl]amino methane) in order to maintain the pH. As shown in FIG. 4, the lactic acid 54 is deposited in solution in the first chamber 40 and the NAD/buffer in solution 56 is deposited in second chamber 42 in measured amounts while the cover 14 is removed. These solutions fill these chambers over the level of the orifices 30 and extend a short distance into the passageway 32a, one having more head than the other. The solutions are deposited either separately or simultaneously and in so doing entrap air in the passageway 32a which acts as a barrier between the liquids. The chamber contents are lyophilized or freeze dried and an atmosphere of inert gas or dry air is added after which the cover 14 is secured in position on the lip 50 of the main body 10. The reagents may be stored in this condition for considerable periods of time or the cuvette may be used immediately for analysis. The lyophilized lactic acid 58, or trigger reagent, and the lyophilized NAD reagent 60 are shown in FIG. 5, in which condition the reagents are in the form of cakes which adhere to the upward projections 48 from the bottoms of the respective chambers. Further, in this condition, the lyophilized reagents 58, 60 may extend a short distance through the respective orifices 30. The passageway 32a isolates such lyophilized reagents.

When the analysis is to be performed, a hypodermic needle indicated by arrow 62 (FIG. 3) aspirates (not shown) a predetermined amount of blood serum from a suitable source and subsequently punctures the cover in the area of chamber 42 to introduce such blood serum into the last mentioned chamber in a single injection, together with a quantity of a diluent, which in this instance is water to reconstitute the lyophilized reagent in the chamber, the reconstituted reagent being indicated at 64 as shown in the last-mentioned view. Substantially simultaneously (or separately), with the dispensing in chamber 42 the hypodermic needle indicated by an arrow 66 in the last-mentioned view, having punctured the cover 12 in the area of the chamber 40, dispenses water as diluent for this analysis in the proper volume in that chamber to reconstitute the lyophilized reagent therein. The last-mentioned reconstituted reagent is indicated at 68. The reagents remain isolated from each other by air trapped in the passageway 32a. In the serum determination under discussion, the relative amounts of the serum, lactic acid reagent, and the NAD reagent which enter into the aforementioned reaction have been disregarded in illustrating the heights to which the chambers 40 and 42 are filled, which heights are purely by way of illustration and not necessarily those used in practice in the particular analysis under discussion.

The fluid contents of the chambers 40, 42 are then incubated under temperature-controlled conditions to be brought to the desired reaction temperature which is usually 30° or 37° C. Subsequent to such incubation, a hollow probe, indicated by an arrow 70 in FIG. 2, may puncture the cuvette cover 14 in the area over the chamber 42, for example to alternately apply air under pressure and create a vacuum sufficient to dislodge from the passageway 32a any solids (such as reagents not completely dissolved) and the air trapped in the upper portion thereof so as to permit the free flow of liquid from one chamber to the other through the passageway during mixing, the cover 14 over the chamber 40 being suitably vented to atmosphere. As many cycles of applied pressure and vacuum may be employed as required for such mixing of the chamber contents. The orifices 30 may be approximately 0.065 inch in diameter, for example, and the groove 32 forming part of the inverted U-shaped passageway 32a may have approximately the same cross-sectional dimension of each orifice 30.

The passageway 32a is of an effective height exceeding the highest filling level of each chamber by a distance at least as great as any capillary rise in the passageway 32a beyond such level of the particular liquid in that chamber. Three considerations should be made in the determination of the proper longitudinal and cross-sectional dimensions of the passageway 32a. The first of these is that the passageway 32a should be as short as possible between the chambers 40, 42 for mixing in the shortest possible time. The volume transferred from one chamber to the other chamber in one half of the aforementioned cycle should be as large as possible. The second consideration is that the passageway 32a of inverted U-shape should be of an effective height to isolate the contents of the chambers under all conditions until intentional mixing of the chamber contents takes place. The third consideration is that the passageway 32a should have the least possible resistance to the free flow of liquid between the chambers during mixing. Obviously, these considerations do not lend themselves one to another but these considerations lead to an optimization of the cross section and length of passageway 32a for given conditions such as, for example, desired barrier effect, duration of mixing cycle and liquid-fill volumes. Subsequent to such mixing, the liquid levels in the chambers are substantially the same as shown in FIG. 2.

It is to be noted that during back-and-forth mixing of the chamber contents, the entry of liquid flowing into each chamber through the corresponding orifice 30 is tangential to an imaginary circle, of substantial radius, the center of which is located in the center of the bottom of the chamber. This produces a rotary and spiral flow of liquid into the chamber, and the provision of the upwardly projecting cone 48 in the center of the chamber bottom aids mixing by eliminating a stagnant portion in the flow in the central region of such rotary flow, thereby enhancing the rate of mixing.

When the mixing of the chamber contents has been completed, any lactic dehydrogenase in the blood serum sample acts as a catalyst which catalyzes the reaction to form as reaction products pyruvic acid and NADH. Since NADH which is produced as a reaction product, has a substantially higher optical density than does NAD, the rate of any increase in optical density is a function of the amount of lactic dehydrogenase in the sample. After the initiation of the reaction as the result of comingling the substrate with the other reaction components, the reaction rate may be determined by placing the cuvette in a position with reference to a nonillustrated photometric analyzer wherein light from a source at a wavelength of 340 nm passes through the transparent windows 18, 24 of the cuvette and through the thickness of the reaction mass between the two windows. Any change in optical density per unit of time may be measured and the data thus obtained may be translated into values indicative of the quantity of lactic dehydrogenase contained in the serum sample.

Figure 9:
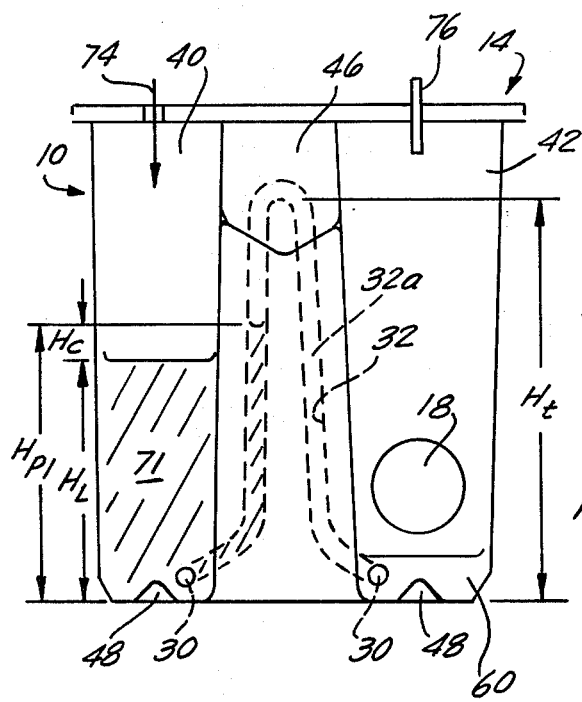
FIGS. 9 and 10 are schematic views illustrating the effectiveness of the barrier isolating liquids in chambers of the cuvette under different conditions.
Figure 10:
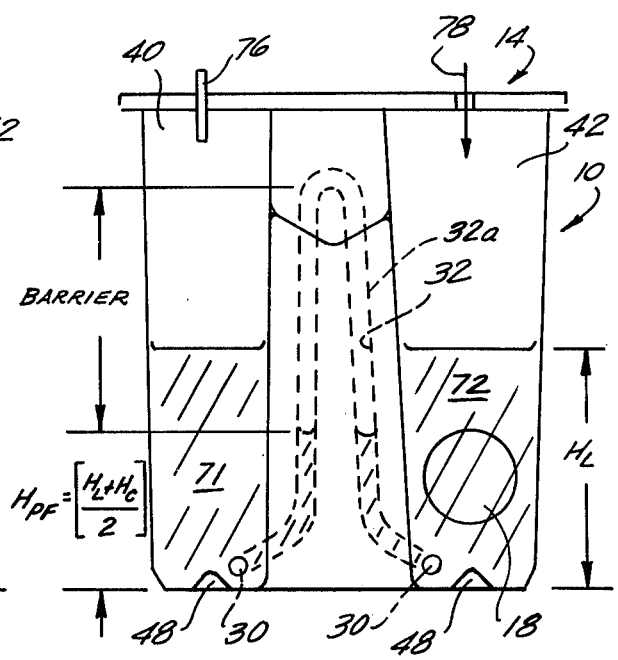

FIGS. 9 and 10, as previously indicated, illustrate the effectiveness of the passageway 32a as a barrier isolating liquids in the chambers 40, 42, under different conditions, prior to any intentional mixing of liquids of said chambers. FIG. 9 illustrates a technique of reconstituting the lyophilized reagent in the chamber 40 to its completion prior to reconstituting the lyophilized reagent 60. FIG. 10 illustrates the barrier condition subsequent to separate reconstituting of the lyophilized reagent 60 in chamber 42, including the addition of the serum sample in the chamber 42 with the reconstituting medium. For simplicity of illustration and description, the final fill levels in chambers 40, 42 are the same.

As previously indicated, the passageway 32a of the cuvette is of an effective height exceeding the highest filling level of each chamber by a distance at least as great as any capillary rise in the passageway beyond such level of the particular liquid in that chamber. Such capillary rise in the passageway 32a will depend upon the cross-sectional dimension of the passageway 32a and the degree to which the particular liquid wets the internal surface of the passageway 32a. In both FIGS. 9 and 10, it is assumed that both chambers 40, 42 are vented to the atmosphere during the filling. As known in the art, these chambers may be vented in a variety of ways. By way of example only, in FIGS. 9 and 10, respectively, dispensing probes which puncture the cover 14 to enter the chambers 40, 42, respectively, may be of the self-venting type indicated by arrows 74, 78 respectively. For example, in FIG. 9, chamber 42 is vented by tube 76 open to the atmosphere and penetrating the cover, while in FIG. 10 the tube 76 is shown penetrating the cover over the chamber 40 to vent the latter. In FIG. 9, $H_{pi}$ indicates the initial liquid height in the leg of the passageway 3a near the chamber 40, the reconstituted reagent being indicated at 71. As shown in FIG. 9, $H_t$ indicates the effective height of the inverted U-shaped passageway 32a and $H_c$ indicates capillary rise in the near leg of the passageway 32a with respect to a filling level $H_1$ in the chamber 40. The foregoing assumes that during the filling of chamber 40 to the last-mentioned level therein, which level is by way of example only, air is free to pass through the passageway 32a including any lyophilized reagent 60 extending into the passageway 32a. If, in fact, lyophilized reagent 60 does not allow free air passage through the passageway 32a on reconstituting of the reagent in chamber 40, $H_c$ is reduced or eliminated. For this reason, among others, $H_c$ may not be a factor.

Subsequent to the filling of chamber 42, to the level indicated, to effect the reagent-sample mixture 72 in FIG. 10, the height of the reconstituted reagent 71 in the near leg of the passageway 32a is reduced as indicated by a comparison of FIGS. 9 and 10, and the levels in both legs of the passageway in this example are the same and less than the filling heights in the chambers 40, 42. As shown in FIG. 10, $H_{pf}$ is equal to $H_1 + H_c/2$: The effective barrier to mixing provided in the passageway 32a is that shown in the last-mentioned view or $H_t$-$H_{pf}$. When the chambers 40, 42 are filled as aforesaid to the same filling levels of FIG. 10 but in a nonillustrated simultaneous manner through nonillustrated twin vented probes extending through the cover 14, $H_{pf}$ is substantially reduced and there is no rise at any time in such filling in the legs of the passageway 32a beyond the last-mentioned filling levels. The same result is achieved when the last-mentioned twin dispensing probes commence filling the chambers 40, 42 substantially at the same time, that is, so that the orifices 30 are covered by the dispensed liquid at approximately the same time. FIGS. 3–5 illustrate liquid and solid heights in the chambers 40, 42 and in the legs of the inverted U-shaped passageway 32a when the chambers 40, 42 are loaded substantially simultaneously and to different levels. Obviously, the cuvette may be utilized without the above-described reagent lyophilization and reconstitution steps, as by initially filling chambers 40, 42 to the liquid levels of FIG. 3 for example. With the liquid filling levels shown in the last-mentioned view, the cuvette may be tilted accidentally, right or left, within a substantial range of angles without loss of the barrier effect of passageway 32a. As shown in FIG. 7, the inverted U-shaped passageway 32a has a compound cross section where each orifice 30 communicates with the respective leg portion of such passageway. As indicated by the last-mentioned view, when compared to FIG. 3 for example, the passageway 32a has a horizontal cross section of greatest dimension substantially less than the horizontal cross section of smallest dimension of either of the chambers 40, 42.

While the preferred embodiments of the cuvette have been illustrated and described, it will be apparent, especially to those versed in the art, that the cuvette may take other forms and is susceptible to various changes in details without departing from the principles of the invention.

What is claimed is:

1. A cuvette body, comprising: means defining first and second upright laterally-spaced liguid-receiving chambers at least one of which has an inlet, passageway means interconnecting lower portions of said chambers, said passageway means having a horizontal cross-section of greatest dimension substantially less than the horizontal cross-section of smallest dimension of either of said chambers and sufficient to normally allow substantially free flow of liquid between said chambers, said passageway means being of inverted U-shape and having an effective height to normally isolate the contents of said chambers.

2. An article as defined in claim 1, wherein: said chamber-defining means further defines respective upward inlet openings in said chambers.

3. An article as defined in claim 1, wherein: said chamber-defining means further defines a pair of at least wall portions of one of said chambers which wall portions are transparent and oppositely disposed for optical analysis of the contents of said one of the chambers.

4. An article as defined in claim 1, wherein: said passageway means is of substantially uniform cross section throughout its length.

5. An article as defined in claim 1, wherein: the upper portion of said inverted U-shaped passageway means is formed on a radius.

6. An article as defined in claim 1, further including means defining a generally conical upward projection from the central bottom region of at least one of said chambers, one end of said passageway means being generally tangential to an imaginary circle of substantial radius in said one of said chambers, the center of said circle being substantially on the vertical axis of said one of said chambers.

7. An article as defined in claim 1, wherein: said passageway means is formed in part in a planar member.

8. An article as defined in claim 7, wherein: said chamber-defining means comprises a main body, said planar member being an external cover member in fixed relation to said main body.

9. An article as defined in claim 8, wherein: said part of said passageway means defined in said cover member is formed as a groove of inverted U-shape in one face of said member.

10. An article as defined in claim 9, wherein: said groove has a cross-sectional shape formed on a radius.

11. An article as defined in claim 10, wherein: a portion of the length of said inverted U-shaped passageway means is formed between an external wall surface of said main body and said cover member.

12. An article as defined in claim 11, wherein: said passageway means comprises a pair of orifices extending through said external wall of said main body and in communication with the respective ones of said chambers and legs of said u-shaped passageway means.

13. An article as defined in claim 1, wherein: said chambers have fill levels above said lower portions and said passageway means has a height exceeding such fill levels which is, at least, in excess of any capillary rise when liquid of controlled volume is introduced into at least one of said chambers.

14. An article as defined in claim 1, further including lyophilized reagent contained in, at least, one of said chambers.

15. An article as defined in claim 14, wherein: said chambers contain an inert atmosphere and further including means for sealing said chambers.

16. An article as defined in claim 1, wherein: the central portion of said passageway has a height which approaches the level of said inlet.

17. An article as defined in claim 1, wherein: at least one of said chambers being adapted to be pressurized to support the flow of liquid from said one chamber to the other of said chambers.

18. An article as defined in claim 1, wherein: at least one of said chambers being adapted to be evacuated to support the flow of liquid from the other of said chambers to said one chamber.

* * * * *